United States Patent [19]

von Angerer et al.

[11] Patent Number: 4,661,511

[45] Date of Patent: Apr. 28, 1987

[54] 2-(HYDROXY-PHENYL)-INDOLES AND PROCESS FOR THEIR PRODUCTION

[75] Inventors: Erwin von Angerer, Regenburg; Helmut Schonenberger, Pentling, both of Fed. Rep. of Germany

[73] Assignee: Degussa Aktiengesellschaft, Frankfurt, Fed. Rep. of Germany

[21] Appl. No.: 635,198

[22] Filed: Jul. 27, 1984

Related U.S. Application Data

[62] Division of Ser. No. 408,898, Aug. 17, 1982, Pat. No. 4,543,360.

[30] Foreign Application Priority Data

Sep. 10, 1981 [DE] Fed. Rep. of Germany ....... 3135841

[51] Int. Cl.[4] .................... C07D 209/32; A61K 31/40
[52] U.S. Cl. .................................. 514/415; 548/509; 548/510; 548/511
[58] Field of Search ............... 548/509, 494, 510, 511; 514/415

[56] References Cited

U.S. PATENT DOCUMENTS

| | | | |
|---|---|---|---|
| 3,159,646 | 12/1964 | Millionis et al. | 548/260 |
| 3,214,436 | 10/1965 | Boyle et al. | 548/260 |
| 3,870,519 | 3/1975 | Piller | 544/214 |
| 3,907,700 | 9/1975 | Grier | 548/306 |
| 3,978,074 | 8/1970 | Jancis et al. | 548/260 |
| 4,017,508 | 4/1977 | Pond | 548/511 |
| 4,057,530 | 11/1977 | Pigerol et al. | 548/511 |
| 4,113,736 | 9/1978 | Pigerol et al. | 548/511 |
| 4,129,572 | 12/1978 | Pigerol et al. | 548/511 |

FOREIGN PATENT DOCUMENTS

| | | | |
|---|---|---|---|
| 1488464 | 10/1977 | United Kingdom . | |
| 1487659 | 10/1977 | United Kingdom . | |
| 1489685 | 10/1977 | United Kingdom . | |
| 1522894 | 8/1978 | United Kingdom | 548/511 |
| 1541957 | 3/1979 | United Kingdom . | |

OTHER PUBLICATIONS

Duncan, et al., "P(2-Indolyl)Phenylacetic Acids," Chem. Abst. 78: 136058(t), 1973.
Bazile, et al., "... 2-Phenyl-3-Mercaptoindole," Chem. Abst. 88: 190695(t), 1978.
Ariens, E. J., *Drug Design*, Academic Press, New York (1971), pp. 10–11.
McOmie, J. F. W., *Protective Groups in Organic Chemistry*, Plenum Press (1973), pp. 145–147 & 171–172.
Epstein, et al., "Production of Melanomas from DMBA-induced Blue Nevi . . . With Ultraviolet Light," *Chem. Abst.* 66: 53653j (1967).
Chemical Abstract, vol. 86, Item 171257u (1977).
Chemical Abstract, vol. 84, Item 122827e (1976).

*Primary Examiner*—Mark L. Berch
*Assistant Examiner*—G. Hendricks
*Attorney, Agent, or Firm*—Cushman, Darby & Cushman

[57] ABSTRACT

Pharmaceutical compositions are provided containing a 2-(hydroxyphenyl)-indole or a 2-($C_2$-$C_6$-alkanoxyloxyphenyl) indole and a pharmaceutically acceptable carrier.

21 Claims, No Drawings

2-(HYDROXY-PHENYL)-INDOLES AND PROCESS FOR THEIR PRODUCTION

BACKGROUND OF THE INVENTION

This is a division of application Ser. No. 408,898, filed Aug. 17, 1982, now U.S. Pat. No. 4,543,360.

In the J. Med. Chem. Vol. 9 (1966), pages 527–536 there is described antiphlogistically active 2,3 bis (p-methoxyphenyl)indole. Additionally, in this literature there is also mentioned the two compounds 2-(4-methoxyphenyl)-indole and 2-(4-methoxyphenyl)-3-methyl indole whereby there is likewise stated an antiphlogistic activity for the latter compound. Furthermore, there are known the following indole compounds as starting materials for the production of other indole compounds: 2-(4-hydroxy-phenyl)-indole, 2-(4-methoxyphenyl-5-methoxy)-indole, 1-methyl-2-(4-methoxyphenyl)-indole, 1-ethyl-2(3,4-dihydroxyphenyl)-indole, 1-ethyl-2-(3,4-dimethoxy-phenyl)-indole, 1-propyl-2(4-propoxyphenyl)-6-methoxy-indole, and 2-(3,5-dimethoxy-phenyl)-5-methoxy-indole. In this connection see J. Chem. Soc. Vol. 59 (1963), pages 4593–4595, Aust. J. Chem. Vol. 28 (1975), pages 65–80; Belgian Pat. No. 621047 and U.S. Pat. No. 3,023,221.

BRIEF DESCRIPTION OF THE INVENTION

The invention is directed to compounds of formula I, their method of preparation and their use as pharmaceuticals. While some of the compounds are old per se and are excluded from the claims to the compounds and from some of the methods of preparation all of the compounds are suitable for the pharmaceutical uses.

According to the invention there are employed for the pharmaceutical uses compounds of general formula (I)

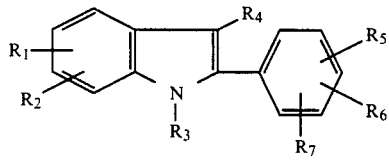

where the groups $R_1$, $R_2$, and $R_6$ are the same or different and are hydrogen, a hydroxy group, a $C_1$–$C_6$ alkoxy group, e.g. methoxy, ethoxy, propoxy, isopropoxy, butoxy, sec.butoxy, amyloxy, or hexoxy or a $C_2$–$C_6$-alkanoyloxy group, e.g. acetoxy, propionoxy, butyroxy, valeroxy, or caproxy, the groups $R_2$ and $R_6$ also can be a halogen, e.g. chlorine, bromine, or fluorine, $R_3$ and $R_4$ are the same or different and are hydrogen or a $C_1$–$C_6$-alkyl group, e.g. methyl, ethyl, propyl, isopropyl, butyl, sec.butyl, amyl, hexyl, $R_5$ is a hydroxy group, a $C_1$–$C_6$-alkoxy group, e.g. methoxy, ethoxy, propoxy, isopropoxy, butoxy, sec.butoxy, amyloxy, or hexoxy or a $C_2$–$C_6$-alkanoyloxy, e.g. acetoxy, propionoxy, butyroxy, valeroxy, or caproxy and $R_7$ is hydrogen or a halogen atom, e.g. chlorine, bromine, or fluorine.

For the most part these are new compounds. However, the following compounds are excluded from the compound claims: 2-(4-hydroxy-phenyl)-indole, 2-(4-methoxy-phenyl)-indole, 2-(3,4-dimethoxy-phenyl)-indole, 2-(3,4-diethoxy-phenyl)-indole, 2-(4-methoxy-phenyl)-3-methyl-indole, 2-(4-hydroxy-phenyl)-5-methoxy-indole, 2-(4-methoxy-phenyl)-5-methoxy-indole, 1-methyl-2-(4-methoxy-phenyl)indole, 1-methyl-2-(3,4-dipropyloxy-phenyl)-indole, 1-ethyl-2-(3,4-dihydroxy-phenyl)-indole, 1-ethyl-2-(3,4-dimethoxy-phenyl)-indole, 1-methyl-2-(4-methoxy-phenyl)-7-methoxy-indole, 1-propyl-2-(4-propyloxy-phenyl)-6-methoxy-indole, and 2-(3,5-dimethoxy-phenyl)-5-methoxy-indole.

The compounds of formula I can be prepared by either (a) condensing a compound of the formula

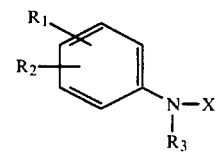

where $R_1$, $R_2$, and $R_3$ are as defined above and X is hydrogen or an amino group with a compund of the general formula

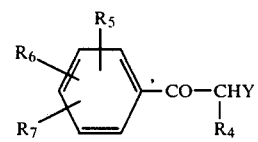

where $R_4$, $R_5$, $R_6$, and $R_7$ are as defined above and Y is a halogen atom, e.g. chlorine, bromine, or fluorine, a hydroxy group, a pyridinium group, or together with the hydrogen atom the $N_2$ group in case X is hydrogen or wherein Y is hydrogen in case X is the amino group with indole ring closure, or (b) heating a compound of the general formula

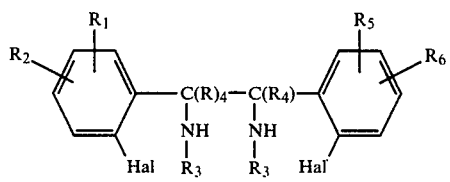

where $R_1$, $R_2$, $R_3$, $R_4$, $R_5$, and $R_6$ are as given above and Hal is chlorine, bromine, or iodine, or (c) heating a compound of the general formula

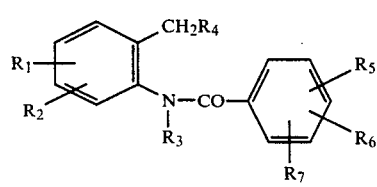

in the presence of an alkali alcoholate, e.g. sodium methylate, potassium methylate, sodium ethylate, potassium ethylate, sodium propylate, or sodium butylate, or an alkali amide, e.g. sodamide or potassium amide, or (d) reducing a compound of the general formula

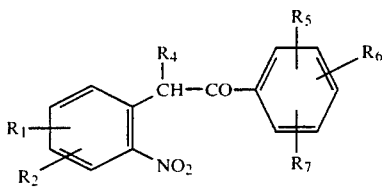

and optionally alkylating and/or splitting off an ether group present and/or acylating a hydroxy group present and/or splitting off an acyl group present.

The pharmaceutical compositions of the invention contain the compound of formula I together with a customary pharmaceutical carrier and/or a diluent.

The compounds of the invention have only slight estrogenic properties but have strong antiestrogenic properties (for example, on the uterus of the mouse). The compounds of the invention have a marked affinity for the oestradiol receptor, by displacing the $^3$H-17$\beta$-oestradiol from the receptor and have a retarding action on the growth of tumor cells, especially retarding the growth of hormone dependent mammary tumor cells. For example, the compounds of the invention retard the tumor growth of the 7,12-dimethyl benzanthracene (DMBA) induced hormone dependent mammary carcinoma of the Sprague-Dawley rat and for example, are suited for the therapy of hormone dependent tumors (for example, mammary carcinomas, endometrium carcinomas, prostate carcinomas, melanomas). Furthermore, they also have a cytostatic action on hormone independent carcinoma cells (for example on hormone independent mammary carcinoma cells).

The pharmacological activity is true both for the new compounds and the old compounds embraced by formula I.

In the compounds of formula I the $C_1$-$C_6$ alkyl groups, $C_2$-$C_6$ alkanoyloxy groups, or $C_1$-$C_6$ alkanoyloxy groups can be straight or branched. Especially it is a matter with alkyl groups of methyl, ethyl, propyl, or butyl groups, with the alkoxy groups of methoxy, ethoxy, or propoxy groups and with the alkanoyloxy group of acetyl propionyl, or butyryl groups. In case the compounds of formula I contain halogen atoms it is a matter especially of chlorine, bromine, or fluorine atoms.

For example, such compounds of formula I posses a good antitumor action where $R_1$ is a hydroxy group or a $C_2$-$C_6$-alkanoyloxy group in the 5 or 6 position of the indole ring and $R_5$ is a hydroxy group or a $C_2$-$C_6$-alkanoyloxy group in the 4-position of the phenyl ring, $R_3$ is a $C_1$-$C_4$ alkyl group (especially a $C_1$-$C_3$-alkyl group) and $R_4$ is hydrogen or a $C_1$-$C_6$-alkyl group (especially a $C_1$-$C_3$ alkyl group) and $R_2$ is hydrogen, a hydroxy group or $C_2$-$C_6$ alkanoyloxy group in the 3-position or a halogen in the 2-position of the phenyl ring. Especially such compounds of formula I are of significance wherein the groups $R_1$ and $R_5$ are the same or different and are a hydroxy group or a $C_2$-$C_6$-alkanoyloxy group, in which case $R_1$ is located in the 5 or 6 position of the indole ring and $R_5$ is located in the 4-position of the phenyl ring, $R_3$ is a $C_1$-$C_3$-alkyl group, $R_4$ is hydrogen or a $C_1$-$C_3$-alkyl group and the remaining $R_2$, $R_6$, and $R_7$ are hydrogen.

Furthermore, compounds of formula I are of significance wherein the groups $R_1$ and $R_5$ are the same or different and are a hydroxy group or a $C_2$-$C_6$-alkanoyloxy group, whereby $R_1$ is in the 5 or 6-position of the indole ring and $R_5$ is in the 4-position of the phenyl ring, $R_3$ is a $C_1$-$C_3$ alkyl group, $R_4$ is hydrogen or a $C_1$-$C_3$ alkyl group, $R_2$ is a halogen (especially Cl) in the 4-position of the indole ring and $R_6$ and $R_7$ are the same or different and are hydrogen or halogen (esecially Cl) is the 2 or 2 and 6 positions of the phenyl ring.

The formula I also includes the possible enantiomers and diastereomers. In case the compounds are racemates these can be split into the optically active isomers in known manner, for example by means of an optically active acid, e.g. D-tartaric acid or L-tartaric acid. However, it is also possible to add previously prepared enantiomers, or in a given case, also diastereometric starting material, whereby then there is obtained as end product a correspondingly pure optically active form or diastereometric configuration.

There can be introduced a $C_1$-$C_6$ alkyl group into the product of formula I where the group $R_3$ is hydrogen. This alkylation takes place in known manner. As alkylating agent there can be employed for example esters of the formula alkyl Hal where Hal is a halogen atom (especially chlorine, bromine, or iodine, e.g. methyl chloride, methyl bromide, methyl iodide, ethyl chloride, ethyl bromide, ethyl iodide, propyl iodide, propyl bromide, butyl iodide, amyl iodide, or hexyl iodide, Ar SO$_2$O alkyl where Ar is an aromatic group as for example, a phenyl or naphthyl group which in a given case, may be substituted by one or more lower alkyl groups, e.g. p-toluene sulfonic acid, $C_1$-$C_6$-alkyl ester, or chlorine or bromine, e.g. methyl benzenesulfonate, ethyl benzenesulfonate, butyl benzenesulfonate, methyl p-toluenesulfonate, ethyl p-toluenesulfonate, 1-methyl naphthalenesulfonate, 2-methyl naphthalene sulfonate, methyl p-chlorobenzenessulfonate, or ethyl p-bromobenzenessulfonate, and SO$_2$ (O alkyl)$_2$ where alkyl is a $C_1$-$C_6$ alkyl group, e.g. dimethyl sulfate or diethyl sulfate and the like. The alkylation reaction in a given case is carried out under addition of customary acid binding agents, such as alkali carbonates (e.g. K$_2$CO$_3$ and Na$_2$CO$_3$), alkali metal hydroxides (e.g. NaOH and KOH), pyridine or other customary tertiary amines, e.g. N,N-dimethyl aniline and triethyl amine, at a temperature between 0° and 200° C., preferably 20° to 150° C. in an inert solvent such as lower alcohols (e.g. methanol, ethanol, isopropanol), lower ketones (e.g. acetone, methyl ethyl ketone), lower haloalkanes (e.g. chloroform, methylene chloride, dichloroethane), dioxane, dimethyl formamide, dimethyl sulfoxide, aromatic hydrocarbons (e.g. benzene, toluene, xylene) or pyridine. However, in this alkylation the procedure can be to first product an alkali compound of the formula I to be alkylated by reacting it in an inert solvent such as dioxane, tetrahydrofuran, dimethyl formamide, benzene, toluene, or xylene or in liquid ammonia with an alkali metal (e.g. sodium or potassium), alkali hydride (e.g. sodium hydride or potassium hydride) or alkali amide (e.g. sodamide or potassium amide), especially sodium or a sodium compound, at a temperature between −70° and +120° C. and then adding the alkylating agent (for example $C_1$-$C_6$ alkyl iodide or $C_1$-$C_6$-alkyl bromide) at a temperature between −70° and 30 50° C.

Furthermore, there can be introduced into compounds of formula I wherein $R_4$ is hydrogen, a $C_1$-$C_6$ alkyl group. This alkylation for example can take place with an aliphatic saturated $C_1$-$C_6$ aldehyde, e.g. formaldehyde, acetaldehyde, propionaldehyde, butyraldehyde, valeraldehyde, or caproaldehyde, at a temperature of about 0° C. in a lower alcohol (e.g. methanol, ethanol) in the presence of an acid (hydrogen halide, e.g. hydrogen chloride, hydrogen bromide, or hydrogen iodide, sulfuric acid, or acetic acid) analogous to J. Org. Chem. Vol. 22 (1957) 1134. From the primary alcohols formed in this reaction there arise by the splitting off of water the corresponding unsaturated compounds, which for example, in the presence of noble metal catalysts, e.g. palladium, or platinum, are hydrogenated in a customary solvent (e.g. methanol) for this purpose. However, it is also possible to introduce $R_4$ by reaction of a compound of formula I wherein $R_4$ is hydrogen with an $\alpha,\beta$-unsaturated $C_4$-$C_6$-ketone (e.g. butenone) or the $C_1$-$C_6$-alkyl ester of an $\alpha,\beta$-unsaturated $C_3$-$C_6$-carboxylic acid (e.g. methyl acrylate, ethyl acrylate, butyl acrylate, hexyl acrylate, methyl ethylacrylate, methyl crotonate) at a temperature between 50° C. and 200° C. in a solvent such as acetic anhydride/glacial acetic acid (see J. Chem. Soc. Vol. 79 (1957), pages 2819–2821) and subsequent reduction of the keto or carbalkoxy group with, for example, $LiAlH_4/AlCl_3$ in absolute ether at room temperature (see Kraak et al, Tetrahedron, Vol. 24 (1968), pages 3381–3398).

Products of formula I wherein one or more of the groups $R_1$, $R_2$, $R_5$, and $R_6$ represents a hydroxy group can be acylated on the hydroxy group by a $C_2$-$C_6$ alkanoyl group. This acylation can take place in an inert solvent or suspension agent such a dioxane, dimethyl formamide, benzene or toluene at a temperature between 0° and 200° C., preferably 20° to 150° C. As acylating agent there can be used ketene as well as acid halides (chloride, bromide, iodide), e.g. acetyl chloride, acetyl bromide, acetyl iodide, propionyl chloride, butyryl chloride, caproyl chloride, acid anhydrides, e.g. acetic anhydride or esters of alphatic carboxylic acids having 2–6 carbon atoms, e.g. methyl acetate, ethyl acetate, butyl acetate, methyl propionate, methyl butyrate, methyl caproate, in a given case with addition of an acid binding agent such as an alkali carbonate, e.g. sodium carbonate or potassium carbonate, an alkali hydroxide, e.g. sodium hydroxide or potassium hydroxide, an alkali alcoholate, e.g. sodium methylate, potassium methylate or sodium ethylate or a tertiary amine, for example, triethyl amine or pyridine. Pyridine also can be used simultaneously as solvent. With the esters it is especially a matter of those of the above-mentioned carboxylic acids with lower aliphatic alcohols. The acylation can also be carried out in such manner that first there is produced an alkali compound of the compound being reacted by reacting it in an inert solvent such as dioxane, dimethyl formamide, benzene or toluene with an alkali metal, alkali hydride or alkali amide (especially sodium or a sodium compound) at a temperature between 0° and 150° C. and then adding the acylating agent.

The $C_2$-$C_6$-alkanoyl groups in the compounds of formula I can be split off again solvolytically, through which the corresponding free hydroxy indole compounds of formula I are obtained. This solvolytic splitting off takes place for example by saponification with dilute acids, e.g. hydrochloric acid or sulfuric acid, or by means of basic materials (potash, soda, aqueous alkali solutions, alcoholic alkali solutions, $NH_3$) at a temperature between 10° and 150° C., especially 20°–100° C.

As solvents or suspension agent for this there can be used: water, lower aliphatic alcohols, e.g. methanol or ethanol, cyclic ethers such as dioxane or tetrahydrofuran, aliphatic ethers, e.g. diethyl ether, dimethyl formamide, etc. as well as mixtures of these agents.

Those compounds of the formula I wherein one or more of the groups $R_1$, $R_2$, $R_5$, and $R_6$ are $C_1$-$C_6$-alkoxy groups can be converted by ether splitting into the corresponding hydroxy compounds. This ether splitting takes place for example without a solvent or in an inert solvent such as boron tribromide, boron trifluoride, aluminum chloride, silicon tetrachloride, aluminum tribromide, sodium methyl-thiolate, $(CH_3)_3SiCl + NaI$ at a temperature between $-70°$ C. and 200° C. As solvent for the ether splitting there can be used for example: aliphatic halohydrocarbons such as for example methylene chloride, aromatic hydrocarbons such as benzene, toluene, xylene, halogenated aromatic hydrocarbons such as chlorobenzene and dichlorobenzene, dimethyl formamide and acetonitrile.

Furthermore, this ether splitting can also take place by mean of concentrated hydroiodic acid, pyridine hydrochloride, hydrobromic acid or methyl magnesium iodide with or without a solvent at a temperature between 20° C. and 250° C., As solvent for this last mentioned splitting there can be used for example aliphatic ethers having alkyl groups of 1–6 carbon atoms, e.g. diethyl ether, dipropyl ether, methyl butyl ether.

The isolation of the thus obtained hydroxy indole suitably takes place via corresponding acyl compounds, for example acetyl compounds. For this purpose the reaction mixture obtained in the ether splitting is extracted with an organic medium which dissolved the indole compound (for example ethyl acetate, chloroform), and the residue obtained after removal of this extraction agent is treated with a lower aliphatic acid anhydride (for example acetic anhydride) in an inert solvent in the presence of a basic material at a temperature between 20° C. and 200° C. In general this acylation takes place in the previously given manner.

It can also be suitable in the stated processes of production to protect hydroxyl groups present in the starting material by known protective groups. Frequently such protective groups are required by the production of the starting compounds themselves. These protective groups are readily split off from the end products. It is a matter of either easily solvolytically splittable acyl groups or hydrogenating splittable groups, as for example, the benzyl group. The solvolytically splittable protective groups are split off for example by saponification with dilute mineral acids (e.g. sulfuric acid or hydrochloric acid) in a solvent or suspension medium (e.g. lower alcohols, e.g. methanol or ethanol) at a temperature between 10° and 150° C. Depending on the type of protective group, however, splitting off even takes place already during the reaction process. The latter for example is the case if the hydroxyl group (or groups) is protected by a benzyl group or the carbobenzoxy group and the process includes a hydrogenation step. If the protective group is not split off during the reaction then a simple post treatment of the reaction product is necessary, whereby then the splitting off of the protective group takes place under conditions such as are stated above.

As protective groups there can be employed for example: benzyl group, 2-phenethyl group, benzene ring substituted benzyl groups, as for example the p-bromo or p-nitrobenzyl group, the carbobenzoxy group, the carbobenzthio group, the trifluoroacetyl group, the phthalyl group, the trityl group, the p-toluene-sulfonyl group, and the like, but additionally there are also suitable simple acyl groups as for example, the tert.-butylcarboxy group.

The splitting off of the benzyl protective group takes place for example through catalytic hydrogenation. As catalysts there can be used for example the customary finely divided metal catalysts such as noble metal catalysts, for example Raney nickel, platinum or especially palladium. The hydrogenation can be carried out at normal temperatures or elevated temperatures. Suitably there is used a temperature range of about 20°–200° C., in a given case under elevated pressure (1–100 bar, especially 1–50 bar). The splitting off of benzyl protective groups or α-phenylethyl groups can also take place under the already given conditions of the ether splitting.

To Process (a)

The process is carried out with or without solvent at a temperature between 20° and 250° C., especially 50° and 200° C. As solvents there can be used for example halogenated aromatic hydrocarbons (e.g. chlorobenzene or dichlorobenzenes), cycloparaffins having 7 to 11 carbon atoms (for example cycloalkane rich petroleum or specific fractions of the petroleum distillation having boiling points from 100° C., as for example naphtha), in a given case, alkyl substituted aromatic hydrocarbon such as benzene, toluene, xylene, methyl-naphthalene, aliphatic alcohols such as ethanol, propanol, tert.-butanol, lower alkanoic acids (e.g. acetic acid or propionic acid), acetonitrile, ethylene glycol, nitrobenzene, cyclic ethers (dioxane), dimethyloxyethane, water or aqueous medium.

It is frequently suitable to carry out the process at acid pH (3 to 4) or in the presence of an acid condensation agent (especially if $X=NH_2$ and $Y=H$). Such condensation agents are, for example, strong organic or inorganic acids or their mixtures, such as hydrogen halides (HCl, alcoholic HCl, HBr), sulfuric acid (such as alcoholic sulfuric acid), phosphoric acid, organic sulfonic acids (especially aromatic sulfonic acids such as benzenesulfonic acid, or p-toluene sulfonic acid), polyphosphoric acid, trichoroacetic acid, acetic acid, or mixtures of acetic acid and a mineral acid (for example, glacial acetic acid/sulfuric acid, glacial acetic acid/hydrohalic acid, especially glacial acetic acid/HCl. Furthermore there can be used as condensation agents zinc chloride, copper (I) chloride, tin (II) chloride, nickel (II) chloride, cobalt chloride, platinum chloride, copper (I) bromide or also the hydrochloride of the aromatic amine employed.

The process is suitably carried out in an inert atmosphere, for example under nitrogen. In case X of the formula II represents the amino group and Y of formula III hydrogen, in a given case, there can be used as condensation agents Grignard reagents, boron trifluoride or cobalt, copper, or nickel powder or cation exchangers, sulfosalicylic acid or polyphosphate $C_1$–$C_6$ alkyl esters.

In case X is $NH_2$ and Y is H it is understood that it is also possible to isolate the primary hydrazone formed and then to carry out the indole ring closure.

In case Y is a pyridinium group, it is preferably a matter of the halide (for example, the chloride or bromide). In case Y and the adjacent hydrogen atom represent the $N_2$ group it is a matter of the corresponding phenyldiazo-alkyl ketone. Such diazoketone for example can be obtained analogous to Blades, Wilds, J. Org. Chem. Vol. 21 (1956), pages 1013–1021.

Insofar as they are not known starting compounds of formula II where X indicates the amino group can be prepared for example as follows: by nitrosation of compounds of formula II where X is hydrogen and reduction of the thus obtained nitroso compounds by means of zinc/glacial acetic acid, sodium/alcohol, $LiAlH_4$ or hydrogen in the present of noble metal catalysts (for this see E. Muller in Houben-Weyl, Methoden der Organischen Chemie Vol. 10/2, pages 1–71, G. Thieme Verlag, Stuttgart, 1967).

Starting materials of formula III where Y is a halgeon atom can be produced for example analogous to W. Bradley, G. Schwarzenbach, J. Chem. Soc. (London), 1928, pages 2904–2912 from the corresponding ($R_4$–$R_7$ groups containing) omega-diazoacetophenones and hydrogen halide. The omega-diazoacetophenones can be obtained from the corresponding benzoyl chlorides and diazomethane in the customary manner. There can be obtained from the thus obtained phenacylhalides those compounds of formula III wherein Y is the hydroxy group, for example by treatment with aqueous barium carbonate solution at 100° C. (see O. Fischer, M. Busch, Berichte der Deutschen Chemischen Gesellschaft, Vol. 24 (1891), pages 2679–2683).

Starting materials of formula III wherein Y represents a pyridinium group can, for example, be obtained by reaction of the corresponding (substituted by the groups $R_4$, $R_5$, $R_6$, and $R_7$) omega-diazoacetophenone with pyridium salts, for example pyridinium halides (see in this connection King, Miller, J. Amer. Chem. Soc. Vol 70 (1948), pages 4154–4160).

To Process (b)

The process is carried out with or without solvent at a temperature between 150° C. and 250° C. As solvent there can be used for example, trichlorobenzene, triethylene glycol, diethyl ether of diethylene glycol.

The starting material for example can be obtained in the following manner: A compound of the general formula

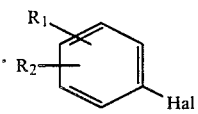   VII by treatment with formaldehyde in acid medium has introduced in the ortho position to the halogen atom a hydroxymethyl group to form a compound of formula VIII

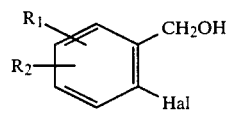   VIII

This hydroxymethyl group is oxidized to the corresponding aldehyde group and the thus obtained aldehyde converted by reaction with an amino ($R_3$–$NH_2$) into the corresponding imine or alkylimine of the formula

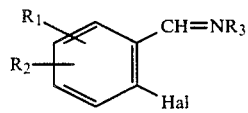   IX

This compound IX is then converted by heating in the presence, for example, of benzpinacol in an inert solvent into compounds of formula IV. Another possibility of converting into compounds of formula IV is the reductive dimerization with aluminum in the presence of HgCl₂ and ethanol in an inert solvent. These reactions take place analogous to the manner given in Example 26 for the production of the starting materials used here.

To Process (c)

The process is carried out with or without a solvent at a temperature of, for example 200° C. to 380° C. The reaction generally lasts for between 10 minutes and 3 hours. In case a solvent is used, for example, there can be employed high boiling N,N-dialkylamines such as N,N-diethylaniline. As amides there can especially be used the alkali amides of ammonia (NaNH₂, KNH₂) or also alkali amides of aromatic amines (for example o-toludine), whereby the alkali metals especially are sodium or potassium.

The starting compounds of formula V can be produced for example analogously to the synthesis of the N-benzoyl-o-toluidide from the corresponding (substituted by the groups R₁, R₂, R₃, and R₄) o-alkyl anilines and the corresponding (substituted by the groups R₅ to R₇) benzoyl chlorides (in this connection see P. Jacobson, L. Huber, Berichte der Deutschen Chemischen Gesellschaft, Vol. 41 (1908), pages 660–671).

To Process (d)

As reducing agent for this process there can be employed for example iron or zinc powder, in glacial acetic acid, iron (II) sulfate or iron (II) hydroxide in ammonia cal aqueous solution, SnCl₂ in hydrochloric acid solution or hydrogen in the presence of hydrogenation catalysts (noble metal catalysts such as platinum or palladium catalysts, Raney nickel). The reduction is generally carried out between 20° and 130° C. In case hydrogen is reduced there is employed for example, a temperature between 20° and 50° C. in a solvent such as saturated aliphatic or alicyclic ether (for example diethyl ether) or an ester of a lower alkanol and a lower aliphatic carboxylic acid (e.g. ethyl acetate). In employing the other mentioned reducing agents preferably there are employed higher temperatures, for example between 50° and 130° C. in a solvent such as glacial acetic acid, hydrochloric acid, aqueous ammonia.

The starting materials of formula VI can be obtained for example analogous to the synthesis of 2′-nitro-desoxybenzoin by nitriting the corresponding (substituted by the groups R₁ to R₇) desoxybenzoins (in this connection see A. Pictet, Berichte der Deutschen Chemischen Gesellschaft Vol. 19 (1886), pages 1063–1066; O. List, Berichte der Deutschen Chemischen Gesellschaft Vol. 26 (1893), pages 2451–2457).

Furthermore, they can be obtained in known manner by reaction of a compound of the formula

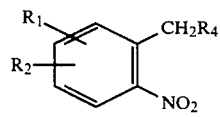

with a compound of the formula

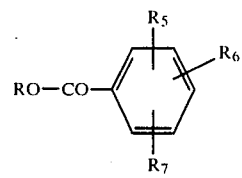

wherein the groups R₁ to R₇ have the stated meanings and R is a C₁–C₆ alkyl group. This reaction takes place for example in a C₁–C₆ dialkyl ether in the presence of an alkali alcoholate (e.g. potassium methoxide, sodium ethoxide) at a temperature between 0° and 100° C.

The compounds according to the invention are suitable for the production of pharmaceutical compositions and preparations. The pharmaceutical compositions or medicaments contain, as active principle, one or more of the compounds according to the invention, optionally in admixture with other pharmacologically or pharmaceutically active substances. The medicaments may be prepared in known manner with the known and usual pharmaceutical assistants, as well as other customary carriers and diluents.

As carriers and assistants, for example, are those recommended or given in the following literature as adjuvants for pharmacy, cosmetic, and related fields such as in Ullmann's Encyklopädie der technischen Chemie, Vol. 4 (1953), pages 1–39; Journal of Pharmaceutical Sciences 52 (1963), pages 918 et seq.; H. v. Czetsch-Lindenwald, Hilfsstoffe für Pharmazie und angrenzende Gebiete; Phar. Ind. 2 (1961), pages 72 et seq.; Dr. H. P. Fiedler, Lexicon der Hilfsstoffe fur Pharmazie, Kosmetik and angrenzende Gebiete, Cantor Kg. Aulendorf in Württemberg (1971).

Examples of such materials include gelatin, natural sugars such as sucrose or lactose, lecithin, pectin, starch (for example cornstarch,), alginic acid, tylose, talc, lycopodium, silica (for example collodial silica), glucose, cellulose, cellulose derivatives for example cellulose ethers in which the cellulose hydroxyl group are partially etherified with lower aliphatic alcohols and/or lower saturated oxyalcohols (for example, methyl hydroxypropyl cellulose, methyl cellulose, hydroxyethyl cellulose), stearates, e.g., methylstearate and glyceryl stearate, magnesium and calcium salts of fatty acids with 12 to 22 carbon atoms, especially saturated acids (for example, calcium stearate, calcium laurate, magnesium oleate, calcium plamitate, calcium behenate and magnesium stearate), emulsifiers, oils and fats, especially of plant origin (for example, peanut oil, castor oil, olive oil, sesame oil, cottonseed oil, corn oil, wheat germ oil, sunflower seed oil, cod-liver oil), mono, di, and triglycerides of saturated fatty acids (C₁₂H₂₄O₂ to C₁₈H₃₆O₂ and their mixtures), e.g., glyceryl monostearate, glyceryl distearate, glyceryl tristearate, glyceryl trilaurate), pharmaceutically compatible mono- or polyvalent alcohols and polyglycols such as glycerine, mannitol, sorbitol, pentaerythritol, ethyl alcohol, diethylene glycol, triethylene glycol, ethylene glycol, propylene glycol, dipropylene glycol, polyethylene glycol 400, and other polyethylene glycols, as well as derivatives of such alcohols and polyglycols, esters of saturated and unsaturated fatty acids (2 to 22 carbon atoms, especially 10 to 18 carbon atoms), with monohydric aliphatic alcohols (1 to 20 carbon atom alkanols), or polyhydric alcohols such as glycols, glycerine, diethylene glycol, pentaerythritol, sorbitol, mannitol, ethyl alcohol, butyl alcohol, octadecyl alcohol, etc., e.g., glyceryl stearate, glyceryl palmitate, glycol distearate, glycol diluarate, glycol diacetate, monoacetin, triacetin, glyceryl oleate, ethylene glycol stearate; such esters of polyvalent alcohols can in a given case also be etherified, benzyl benzoate, dioxolane, glycerine formal, tetrahydrofurfuryl alcohol, polyglycol ethers with 1 to 12 carbon atom alcohols, dimethyl acetamide, lactamide, lactates, e.g., ethyl lactate, ethyl carbonate, silicones (especially middle viscosity dimethyl polysiloxane), magnesium carbonate and the like.

For the production of solutions, there can be used water or physiologically compatible organic solvents, as for example, ethanol, 1,2-propylene glycol, polyglycols, e.g., diethylene glycol, triethylene glycol and dipropylene glycol and their derivatives, dimethyl sulfoxide, fatty alcohols, e.g., stearyl alcohol, cetyl alcohol, lauryl alcohol and oleyl alcohol, triglycerides, e.g., glyceryl oleate glyceryl stearate, glyceryl palmitate, and glyceryl acetate, partial esters of glycerine, e.g., glyceryl monostearate, glyceryl distearate, glyceryl monopalmitate, paraffins, and the like.

In the production of the preparation, there can be used known and customary solution aids or emulsifiers. As solution aids and emulsifiers, there can be used, for example, polyvinyl pyrrolidone, sorbitan fatty acid esters such as sorbitan trioleate, lecithin, gum acacia, gum tragacanth, polyoxyethylated sorbitan monooleate, polyoxyethylated fats, polyoxyoleotriglycerides, linolized oleotriglycerides, polyethylene oxide-condensation products of fatty alcohols, alkylphenols or fatty acids or also 1-methyl-3-(2-hydroxyethyl)-imidazolidone-2. As used herein, polyoxyethylated means that the materials in question contain polyoxyethylene chains whose degree of polymerization generally is between 2 and 40, particularly between 10 and 20.

Such polyoxyethylated materials, for example, can be obtained by reaction of hydroxyl group containing compounds (for example, mono- or diglycerides) or unsaturated compounds such as, for example, those containing the oleic acid radical with ethylene oxide (for example, 40 moles of ethylene oxide per mole of glyceride).

Examples of oleotriglycerides are olive oil, peanut oil, castor oil, sesame oil, cottonseed oil, corn oil (see also Dr. H. P. Fiedler, supra, pages 191-195).

Furthermore, there can be added preservatives, stabilizers, buffers, for example, calcium hydrogen phosphate, collodial aluminum hydroxide, taste correctives, antioxidants and complex formers (for example, ethylene diamine tetraacetic acid) and the like. In a given case for stabilization of the active molecule, the pH is adjusted to about 3 to 7 with physiologically compatible acids or buffers. Generally, there is preferred as neutral as possible to weak acid (to pH 5) pH value.

As antioxidants, there can be used, for example, sodium meta bisulfite, ascorbic acid, gallic acid, alkyl gallates, e.g., methyl gallate and ethyl gallate, butyl hyroxyanisole, nordihydroguararetic acid, tocopherols as well as tocopherol and synergists (materials which bind heavy metals by complex formation, for example, lecithin, ascorbic acid, phosphoric acid). The addition of synergists increases considerably the antioxidant activity of tocopherol. As preservatives, there can be used, for example, sorbic acid, p-hydroxybenzoic acid esters (for example, lower alkyl esters such as the methyl ester and the ethyl ester) benzoic acid, sodium benzoate, trichloroisobutyl alcohol, phenol, cresol, benzethonium chloride, and formalin derivatives.

The pharmacological and galenical treatment of the compounds of the invention takes place according to the usual standard methods. For example, the active material or materials and assistants or carriers are well mixed by stirring or homogenization (for example, by means of customary mixing apparatus, e.g., a colloid mill or ball mill), wherein the operation is generally carried out at temperatures between 20° and 80° C., preferably 20° to 50° C., especially at room temperature. Besides, reference is made to the following standard work: Sucker, Fuchs, Speiser, Pharmazeutische Technologie, Thieme-Verlag Stuttgart, 1978.

The application of active material or drug can take place on the skin or mucous membrane or internally, for example, orally, parenterally, pulmonarily, rectally, nasally, vaginally, perlinqually, intravenously, intraarterially, intracardially, intramuscularly, intraperitoneally, intracutaneously, or subcutaneously.

The addition of other medicines is also possible or favorable, above all, the steroid hormones and/or other cancer chemotherapeutics.

The compounds of the invention show on 7,12-dimethylbenz[a]-anthracene induced hormone dependent mammary carcinoma of the rat a good retarding activity on the growth of established tumors as well as a reduction of the number of new tumors.

For example in the above-mentioned experimental methods at a dosage of 4 mg/kg body weight (rat) the starting tumor area is clearly reduced. Remission rates up to 50% are observed. This effect is better than the known medicine Tamoxifen.

The lowest effective dosage is between 0.5 and 2 mg/kg subcutaneously.

As a general dosage range for the activity from the above-mentioned test methods there can be used for example 0.5 to 20 mg/kg subcutaneously, especially 2 to 6 mg/kg. The compounds of the invention can be employed for example, for the therapy of hormone dependent mammary carcinomas. Further areas of use for example, are in the therapy of endometrium carcinoma, prostate carcinoma and melanoma.

The pharmaceutical preparations generally contain between 10 and 150 mg, preferably 10 to 30 mg of the active component or components of the invention.

The compounds can be delivered in the form of tablets, capsules, pills, dragees, or in liquid form. As liquid forms, there can be used for example, oily or alcoholic or aqueous solutions, as well as suspension and emulsions. The preferred forms of use are tablets which contain between 10 and 30 mg or solutions which contain between 5 and 20% of the active material.

In individual doses, the amount of active component of the invention can be used, for example, in an amount of:

(a) in oral dispensation between 50 and 150 mg, preferably 20 mg.
(b) in parenteral dispensation (for example, subcutaneously or intramuscularly) between 10 and 100 mg, preferably 20 mg.

For example, there is recommended the use of 1 to 5 tablets containing 10 to 30 mg of active ingredient 3 times daily or for example, intramuscularly or subcutaneously the injection 1 to 3 times daily of a 5 to 10 ml ampoule containing 10 to 30 mg of active substance. In oral preparations, the minimum daily dosage for example, is 10 mg; the maximum daily dosage in oral administration should not be over 150 mg.

The acute toxicity of the compounds of the invention in the mouse (expressed by the $LD_{50}$ mg/kg method of Miller and Tainter, Proc. Soc. Exper. Biol. and Med. 57 (1944), pages 261 et seq.) in oral application is above 1000 mg/kg (for example, between 2000 and 3000 mg/kg and even thereover).

Unless otherwise indicated, all parts and percentages are by weight.

The compositions can comprise, consist essentially of, or consist of the materials set forth.

The methods can comprise, consist essentially of, or consist of the steps set forth with the materials shown.

EXAMPLE 1

2-(4-Methoxy-phenyl)-6-methoxy-indole

A solution of 33 grams (0.16 mole) of 4-methoxy-bromacetophenone in 230 ml of xylene was dropped into a mixture of 54.5 grams (0.45 mole) of m-anisidine and 76 ml of N,N-dimethyl aniline which was heated to 170° C. bath temperature. After cooling the mixture was treated with ethyl acetate and extracted by shaking with 2N HCl. The aqueous phase was again terated with ethyl acetate and the combined organic phases extracted by shaking several times with 2N HCl. After washing with water and drying the solvent was removed in a vacuum. The crystalline residue was washed colorless with a little ethyl acetate. Yield: 18.8 grams, M.P. 228°–230° C.

EXAMPLE 2

1-Methyl-2-(4-methoxy-phenyl)-6-methoxy-indole

There were added in portions 0.06 gram atom of sodium to 200 ml of liquid ammonia. At −70° C. there were dropped into the sodamide solution a solution of 8.85 grams (35 mmol) of 2-(4-methoxy-phenyl)-6-methoxy-indole in 100 ml of absolute tetrahydrofuran, stirring continued for one half hour and then there were dropped in 6 grams (42 mmol) of methyl iodide in 30 ml of absolute tetrahydrofuran. After a further 30 minutes there was removed the cold bath and the ammonia allowed to vaporize overnight. The residue was treated carefully with water and then extracted with ether. The organic phase was washed, dried, and the solvent removed on a rotary evaporator. The residue is recrystallized from ethanol. Yield: 8.63 grams, M.P. 163°–166° C.

EXAMPLE 3

1-Methyl-2-(4-acetoxy-phenyl)-6-acetoxy-indole

At −70° C. there were added 3.4 ml (35 mmol) of $BBr_3$ with the injector into a solution of 2.14 grams (8 mmol) of 1-methyl-2-(4-methoxy-phenyl)-6-methoxy-indole in 50 ml of water free methylene chloride. After 30 minutes the cold bath was removed and the mixture stirred overnight. The reaction mixture is carefully poured into a saturated sodium bicarbonate solution with ice cooling. The product is extracted three times with ethyl acetate, the combined organic extracts washed with sodium bicarbonate solution and water, dried and the solvent removed on a rotary evaporator.

There are added 6 grams of acetic anhydride and 6 grams of pyridine to the thus obtained residue and the mixture heated for 2 hours at the boiling point. After cooling the mixture is poured onto ice, extracted with methylene chloride and the organic phase washed twice with 2N HCl. After drying and removal of solvent in the rotary evaporator the residue is chromatographed with methylene chloride via silica and subsequently recrystallized from ethanol. Yield: 1.77 grams M.P. 118°–120° C.

EXAMPLE 4

1-Methyl-2-(4-hydroxyphenyl)-6-hydroxy-indole 0.3 grams of 1-methyl-2-(4-acetoxy-phenyl)-6-acetoxy-indole was dissolved in 20 cc of methanol, treated under nitrogen with 3 ml of 2N aqueous sodium hydroxide and stirred for 2 hours at room temperature. After acidification with 2N hydrochloric acid, the mixture was extracted by shaking with methylene chloride, dried and the solvent removed in a vacuum, the product was brought to crystallization with a little methylene chloride. Yield: 0.21 grams, M.P. 200°–204° C.

In an analogous manner as is described in Examples 1–4 there were obtained the compounds set forth in Table 1 of the following formula:

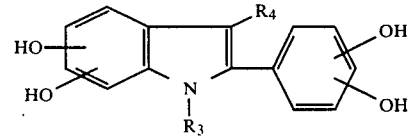

as well as the corresponding diacetates. In case in Table 1 under columns 2 and 3 only one position is given for the phenyl OH or the indole OH this means that the indole or phenyl ring in each case only contains one hydroxy group.

TABLE 1

| Example No. | Position Phenyl—OH | Position Indole—OH | $R_3$ | $R_4$ | M.P. °C. From Methylene Chloride | M.P. of the Diacetate From Ethanol |
|---|---|---|---|---|---|---|
| 5 | 4 | 5 | $C_2H_5$ | H | 163–5 | 163–7 |
| 6 | 4 | 6 | $C_2H_5$ | H | 133–5 | 153–6 |
| 7 | 4 | 6 | $C_3H_7$ | H | 138–40 | 111–2 |
| 8 | 4 | 6 | $C_4H_9$ | H | 117–9 | 99–101 |
| 9 | 3 | 5 | $C_2H_5$ | H | 164–5 | 128–9 |
| 10 | 3 | 6 | $C_2H_5$ | H | 244–6 | 76–8 |
| 11 | 4 | 5 | $CH_3$ | $CH_3$ | 198–200 | 126–8 |
| 12 | 4 | 5 | $C_2H_5$ | $CH_3$ | 178–81 | 146–7 |
| 13 | 4 | 5 | $C_3H_7$ | $CH_3$ | 153–4 | 106–7 |
| 14 | 4 | 5 | $C_4H_9$ | $CH_3$ | 64–6 | 81 |
| 15 | 4 | 6 | $CH_3$ | $CH_3$ | 203–7 | 119–20 |
| 16 | 4 | 6 | $C_2H_5$ | $CH_3$ | 142–3 | 150–2 |
| 17 | 4 | 6 | $C_3H_7$ | $CH_3$ | 141–5 | 108–10 |

TABLE 1-continued

| Example No. | Position Phenyl—OH | Position Indole—OH | R_3 | R_4 | M.P. °C. From Methylene Chloride | M.P. of the Diacetate From Ethanol |
|---|---|---|---|---|---|---|
| 18 | 3 | 5 | $C_2H_5$ | $CH_3$ | 136–8 | 83–5 |
| 19 | 3 | 6 | $C_2H_5$ | $CH_3$ | 162–3 | 106–7 |
| 20 | 4 | 5 | $CH_3$ | $C_2H_5$ | 148–50 | 113–5 |
| 21 | 4 | 6 | $CH_3$ | $C_2H_5$ | 162–3 | 127–9 |
| 22 | 4 | 6 | $C_2H_5$ | $C_2H_5$ | 171–3 | 146–7 |
| 23 | 3 and 4 | 5 | $C_2H_5$ | $CH_3$ | 129–31 | 107–9 |
| 24 | 3 and 4 | 6 | $C_2H_5$ | $CH_3$ | 138–41 | 121–3 |
| 25 | 3 and 4 | 5 and 6 | $C_2H_5$ | $CH_3$ | 164–7 | 125–6 |

In Examples 5–10 analogous to Example 1, there were reacted in each case 0.2 mole of m or p-anisidine with 0.06 mole of 4-methoxy or 3-methoxy-bromoacetophenone and the reaction product obtained analogous to Example 2 alkylated with the corresponding amount of ethyl iodide, propyl iodide or butyl iodide in the 1-position and then according to Example 3 the methoxy groups split off and acetylated and according to Example 4 the two acetyl groups hydrolyzed off.

In Examples 11–19 analogous to Example 1 in each case 0.2 mole of m or p-anisidine was reacted with 0.06 mole of 4-methoxy or 3-methoxy-α-bromopropiophenone, alkylated analogous to Example 2, the methoxy groups split off and acetylated and subsequently the acetyl group split off according to Examples 3 and 4.

In Examples 20–22 analogous to Example 1, in each case 0.2 mole of m or p-anisidine was reacted with 0.06 mole of 4-methoxy-α-bromobutyrophenone, alkylated analogous to Example 2, the methoxy groups split off and acetylated and subsequently the acetyl groups removed according to Examples 3 and 4.

EXAMPLE 26

1-Methyl-2-(2,6-dichloro-4-methoxy-phenyl)-4-chloro-6-methoxy-indole 2.1 grams of meso-N,N'-dimethyl-1,2-bis(2,6-dichloro-4-methoxy-phenyl)-ethylene diamine were heated in a round flask for 15 minutes at 215° C. After cooling the product was chromatographed with petroleum ether/methylene chloride (1:1 by volume) via silica gel. Yield: 1.25 grams, M.P. 146°–148° C.

The starting material was obtained for example as follows:

A mixture of 100 grams of 3,5-dichloroanisole, 30 grams of paraformaldehyde and 1500 ml of concentrated hydrochloric acid after addition of 15.2 ml of concentrated sulfuric acid was heated for 7 hours at 60° C. After cooling, the product was extracted twice with methylene chloride, washed with water, dried over magnesium sulfate and the solvent removed in a vacuum. The oil remaining was treated with 1 liter of aqueous sodium hydroxide and 0.5 liter of dioxane and boiled under reflux with stirring for 4 hours. After cooling it was worked up as above. The residue was treated with a little chloroform whereby the disubstituted product crystallized out and was separated off. The filtrate after concentration was chromatographed on silica gel with petroleum ether (40°–60° C.)/diethyl ether (1:1 by volume). The para substituted product had an $R_f$ value of about 0.6. Yield: 17–75 grams, M.P. 64°–66° C. (petroleum ether).

28 grams of the thus obtained substituted benzyl alcohol were then heated for 10 hours on the water separator in 750 ml of benzene after addition of 60 grams of manganese dioxide. After cooling the solid was filtered off with suction and the solvent removed in a vacuum.

The 2,6-dichloro-4-methoxybenzaldehyde obtained was recrystallized from methanol. Yield: 18–20 grams, M.P. 107°–109° C.

10 grams of 2,6-dichloro-4-methoxybenzaldehyde were dissolved in a little chloroform and there was dropped in a 10% excess of methylamine in a little water. The mixture was stirred for another hour at room temperature, extracted with chloroform, dried over magnesium sulfate and the solvent removed on a rotary evaporator. The oil remaining was distilled in a high vacuum. Yield: 8.0 grams of solidifying oil.

8 grams of the thus obtained 2,6-dichloro-4-methoxybenzaldehyde-methylimine were then boiled under reflux for 24 hours with 13.5 grams of benzopinacol in 180 ml of isopropanol. After removal of the solvent on the rotary evaporator the residue was dissolved in ether and extracted several times with 2N hydrochloric acid. The aqueous phase was made alkaline with 2N aqueous sodium hydroxide and extracted with chloroform. After drying and removal of the solvent or the rotary evaporator the product was recrystallized from ethanol, whereby the meso-diarylethylene diamine was obtained. Yield: 2.5 grams, M.P. 183°–185° C.

EXAMPLE 27

1-Methyl-2-(2,6-dichloro-4-hydroxyphenyl)-4-chloro-6-hydroxy-indole 3.4 ml (35 mmole) of $BBr_3$ were added with a syringe to a solution of 3.0 grams of 1-methyl-2-(2,6-dichloro-4-methoxy-phenyl)-4-chloro-6-methoxy-indole in 50 ml of water free methylene chloride at −70° C. After 30 minutes the cold bath was removed and the mixture was stirred overnight. The reaction mixture under ice cooling was carefully poured into a saturated aqueous sodium bicarbonate solution. The precipitate was filtered off with suction, washed with water and reprecipitated from methanol/water. Yield: 2.4 grams.

In a manner analogous to Example 26 and 27 there were obtained the compounds in Table 2 of the following formula:

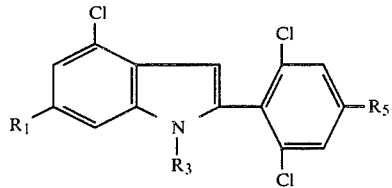

TABLE 2

| Example No. | $R_1$ | $R_3$ | $R_5$ | °C. | Starting Material |
|---|---|---|---|---|---|
| 28 | $OCH_3$ | $C_2H_5$ | $OCH_3$ | 157–158 | |

TABLE 2-continued

| Example No. | $R_1$ | $R_3$ | $R_5$ | °C. | Starting Material |
|---|---|---|---|---|---|
| 29 | OCH$_3$ | C$_3$H$_7$ | OCH$_3$ | 134–136 | |
| 30 | OH | C$_2$H$_5$ | OH | | Compound of Example 28 |
| 31 | OH | C$_3$H$_7$ | OH | 70–72 | Compound of Example 29 |

EXAMPLE OF A PHARMACEUTICAL PREPARATION

Tablets 1.0 kg of the active material (for example, the compound of Example 1) is mixed with 5.0 kg of lactose and the mixture granulated with a solution of 0.15 kg of gelatin in 1.35 kg of water in known manner.

After the mixing in of 0.64 kg of cornstarch as well as 0.21 kg of magnesium stearate there were molded tablets weighing 140 mg and having a diameter of 7 mm and a radius of curvature of 5 mm. The resistance to rupture of the tablets was 60 to 70 Newton (Heberlein-Hardness Tester). Each tablet contains 20 mg of active material.

The entire disclosure of German priority application No. P 3135841.1 is hereby incorporated by reference.

What is claimed is:

1. A compound of the formula:

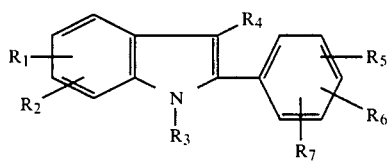

where $R_1$ is hydrogen, a hydroxy group, or a $C_2$–$C_6$-alkanoyloxy group, $R_2$ is hydrogen, a hydroxy group, a $C_2$–$C_6$-alkanoyloxy group or a halogen atom, $R_3$ is a $C_1$–$C_6$ alkyl group, $R_4$ in hydrogen or a $C_1$–$C_6$-alkyl group, $R_5$ is a hydroxy group or a $C_2$–$C_6$-alkanoyloxy group, $R_6$ is hydrogen, a halogen atom, a hydroxy group, or a $C_2$–$C_6$-alkanoyloxy group, and $R_7$ is hydrogen or halogen atom with the proviso that when $R_2$ is hydrogen or halogen $R_1$ must be a hydroxy group or a $C_2$–$C_6$-alkanoyloxy group.

2. A compound according to claim 1 wherein at least one of $R_2$, $R_6$, and $R_7$ is a halogen atom.

3. A compound according to claim 2 wherein all three of $R_2$, $R_6$, and $R_7$ are halogen, $R_1$ and $R_5$ are hydroxy or $C_2$–$C_6$-alkanoyloxy and $R_3$ is hydrogen or $C_1$–$C_6$-alkyl.

4. A compound according to claim 3 wherein $R_2$, $R_6$, and $R_7$ are all chlorine.

5. A compound according to claim 4 wherein $R_2$ is in the 4 position of the indole ring, $R_6$ and $R_7$ are in the 2 and 6 positions of the phenyl ring.

6. A compound according to claim 1 wherein $R_1$ and $R_5$ are hydroxy or $C_2$–$C_6$-alkanoyloxy.

7. A compound according to claim 6 wherein $R_3$ is $C_1$–$C_6$-alkyl and $R_4$ is hydrogen or $C_1$–$C_6$-alkyl.

8. A compound according to claim 6 wherein both $R_1$ and $R_5$ are hydroxy or $C_2$–$C_6$-alkanoyloxy.

9. A compound according to claim 1 wherein the compound is 1-ethyl-2-(2,6-dichloro-4-hydroxyphenyl)-4-chloro-6-hydroxy-indole.

10. A compound according to claim 1 wherein the compound is 1-methyl-2-(2,6-dichloro-4-hydroxyphenyl)-4-chloro-6-hydroxy-indole.

11. A compound according to claim 1 wherein the compound is 1-propyl-2-(2,6-dichloro-4-hydroxyphenyl)-4-chloro-6-hydroxy-indole.

12. A compound according to claim 1 wherein the compound $R_1$ is hydroxy or acetoxy, $R_2$ is chlorine, $R_3$ is a $C_1$–$C_4$ alkyl, $R_6$ and $R_7$ are chlorine, and $R_5$ is hydroxy or acetoxy.

13. A compound according to claim 1 wherein in the compound $R_1$ is hydrogen, hydroxy, or acetoxy, $R_2$ is hydroxy or acetoxy, $R_3$ is $C_1$–$C_4$ alkyl, $R_4$ is hydrogen or $C_1$–$C_2$ alkyl, $R_5$ is hydroxy or acetoxy, $R_6$ is hydrogen and $R_7$ is hydrogen.

14. A compound according to claim 1 wherein $R_5$ is in the 4-position and is hydroxy or a $C_2$–$C_6$-alkanoyloxy group.

15. A compound according to claim 14 wherein $R_5$ is hydroxy or acetoxy.

16. A compound according to claim 15 wherein $R_5$ is hydroxy.

17. A compound according to claim 15 wherein $R_5$ is acetoxy.

18. A compound according to claim 12 wherein $R_5$ is in the 4-position.

19. A compound according to claim 13 wherein $R_5$ is in the 4-position.

20. A compound according to claim 2 wherein $R_5$ is in the 4-position and $R_6$ is hydrogen or a halogen atom.

21. A compound according to claim 3 wherein $R_5$ is in the 4-position.

* * * * *